US011110135B2

(12) United States Patent
Mogna et al.

(10) Patent No.: US 11,110,135 B2
(45) Date of Patent: Sep. 7, 2021

(54) BACTERIAL STRAINS BELONGING TO THE GENUS *BIFIDOBACTERIUM* FOR USE IN THE TREATMENT OF HYPERCHOLESTEROLAEMIA

(71) Applicant: PROBIOTICAL S.P.A., Novara (IT)

(72) Inventors: Giovanni Mogna, Novara (IT); Gian Paolo Strozzi, Novara (IT); Luca Mogna, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 0 days.

(21) Appl. No.: 15/902,977

(22) Filed: Feb. 22, 2018

(65) Prior Publication Data

US 2018/0236014 A1   Aug. 23, 2018

Related U.S. Application Data

(62) Division of application No. 14/117,003, filed as application No. PCT/IB2012/000907 on May 9, 2012, now Pat. No. 9,925,224.

(30) Foreign Application Priority Data

May 9, 2011 (IT) ................ MI2011A0792

(51) Int. Cl.
*A61K 35/745* (2015.01)
*A23L 33/135* (2016.01)
*A23L 29/25* (2016.01)
*A23L 33/21* (2016.01)
*A23L 33/105* (2016.01)

(52) U.S. Cl.
CPC ............ *A61K 35/745* (2013.01); *A23L 29/25* (2016.08); *A23L 33/105* (2016.08); *A23L 33/135* (2016.08); *A23L 33/21* (2016.08)

(58) Field of Classification Search
None
See application file for complete search history.

(56) References Cited

U.S. PATENT DOCUMENTS

| | | | |
|---|---|---|---|
| 3,819,383 A | 6/1974 | Squire et al. |
| 4,187,321 A | 2/1980 | Mada et al. |
| 5,343,672 A | 9/1994 | Kearney et al. |
| 5,413,960 A | 5/1995 | Dobrogosz et al. |
| 5,466,463 A | 11/1995 | Ford |
| 6,221,404 B1 | 4/2001 | Nguyen et al. |
| 6,277,370 B1 | 8/2001 | Vesely et al. |
| 6,479,051 B1 | 11/2002 | Bruce et al. |
| 6,706,347 B1 | 3/2004 | Kurzinger et al. |
| 9,125,768 B2 | 9/2015 | Husmark et al. |
| 9,492,377 B2 | 11/2016 | Mogna et al. |
| 9,883,692 B2 | 2/2018 | Hougee et al. |
| 9,925,224 B2 | 3/2018 | Mogna et al. |
| 10,028,982 B2 | 7/2018 | Mogna |
| 10,286,017 B2 | 5/2019 | Mogna et al. |
| 10,384,847 B2 | 8/2019 | Mogna |
| 10,982,184 B2 | 4/2021 | Mogna |
| 2003/0118571 A1 | 6/2003 | Reid et al. |
| 2005/0017013 A1 | 1/2005 | Peisach et al. |
| 2005/0031814 A1 | 2/2005 | Dawes |
| 2005/0220776 A1 | 10/2005 | Brondstad et al. |
| 2008/0299009 A1 | 12/2008 | Heczko et al. |
| 2009/0041736 A1 | 2/2009 | Sprenger et al. |
| 2009/0061164 A1 | 3/2009 | Pasbrig et al. |
| 2009/0180999 A1 | 7/2009 | Minatelli et al. |
| 2009/0226548 A1 | 9/2009 | Minatelli et al. |
| 2009/0294319 A1 | 12/2009 | Nageli et al. |
| 2010/0003369 A1 | 1/2010 | Ter Haar et al. |
| 2010/0092240 A1 | 4/2010 | Glasser |
| 2010/0168056 A1 | 7/2010 | Troup et al. |
| 2010/0278781 A1 | 11/2010 | Hougee et al. |
| 2011/0020400 A1 | 1/2011 | MacSharry et al. |
| 2011/0236360 A1 | 9/2011 | Ochi et al. |
| 2011/0274722 A1 | 11/2011 | Gorbach et al. |
| 2012/0058095 A1 | 3/2012 | Strozzi et al. |
| 2012/0195868 A1 | 8/2012 | Lathan et al. |
| 2012/0207929 A1 | 8/2012 | Yoo et al. |
| 2014/0065115 A1 | 3/2014 | Mogna et al. |
| 2014/0065116 A1 | 3/2014 | Mogna et al. |
| 2014/0093479 A1 | 4/2014 | Mogna et al. |
| 2014/0105874 A1 | 4/2014 | Mogna et al. |
| 2014/0127164 A1 | 5/2014 | Mogna et al. |
| 2014/0231300 A1 | 8/2014 | Mogna |
| 2014/0328932 A1 | 11/2014 | Mogna |
| 2015/0017128 A1 | 1/2015 | Mogna |
| 2015/0174179 A1 | 6/2015 | Sprenger et al. |
| 2016/0106787 A1 | 4/2016 | Mogna |
| 2016/0184372 A1 | 6/2016 | Mogna |
| 2017/0014335 A1 | 1/2017 | Mogna |
| 2019/0216864 A1 | 7/2019 | Mogna et al. |

FOREIGN PATENT DOCUMENTS

| | | |
|---|---|---|
| CN | 1233474 A | 11/1999 |
| CN | 101432007 A | 5/2009 |
| CN | 101801220 A | 8/2010 |
| CN | 105377277 A | 3/2016 |
| EA | 200200287 A1 | 6/2002 |
| EP | 2364712 A1 | 9/2011 |
| EP | 2707477 B1 | 7/2018 |
| GB | 2396811 A | 7/2004 |
| JP | H11504049 A | 4/1999 |
| JP | 2002507123 A | 3/2002 |

(Continued)

OTHER PUBLICATIONS

Grill et al. Canadian Journal of Microbiology. Oct. 2000, 46, pp. 878-884.*

(Continued)

*Primary Examiner* — Vera Afremova
(74) *Attorney, Agent, or Firm* — Steinfl + Bruno LLP

(57) ABSTRACT

Selected bacterial strains belonging to the genus *Bifidobacterium* for use in the treatment of hypercholesterolaemia are described. In particular, a food composition or supplement product or medical device or pharmaceutical composition has said bacterial strains in association with sterols or phytosterols and/or stanols or phytostanols and/or glucomannan and/or konjac gum and/or prebiotic fibres and/or fermented red rice and/or betaglucans from oats, oat bran, barley, barley bran and/or *Aloe arborescens* gel in lyophilized form.

12 Claims, 3 Drawing Sheets

(56) References Cited

FOREIGN PATENT DOCUMENTS

| | | |
|---|---|---|
| JP | 2002508762 A | 3/2002 |
| JP | 2003522731 A | 7/2003 |
| JP | 2006180836 A | 7/2006 |
| JP | 2009511506 A | 3/2009 |
| JP | 2012527884 A | 11/2012 |
| JP | 2016518441 A | 6/2016 |
| KR | 20130038395 A | 4/2013 |
| RU | 2215656 C2 | 11/2003 |
| RU | 2316586 C2 | 2/2008 |
| RU | 2007147945 A | 7/2009 |
| RU | 2373274 C1 | 11/2009 |
| RU | 2008118418 A | 11/2009 |
| RU | 2445073 C2 | 3/2012 |
| RU | 2465320 C2 | 10/2012 |
| WO | 97/29762 A1 | 8/1997 |
| WO | 97/29763 A1 | 8/1997 |
| WO | 00/35465 A2 | 6/2000 |
| WO | 03/090546 A1 | 11/2003 |
| WO | 2006/082824 A1 | 8/2006 |
| WO | 2006/091103 A1 | 8/2006 |
| WO | 2007/020884 A1 | 2/2007 |
| WO | 2007/050656 A2 | 5/2007 |
| WO | 2007/100765 A2 | 9/2007 |
| WO | WO 2007/125558 * | 11/2007 |
| WO | 2008/107746 A2 | 9/2008 |
| WO | 2010/033768 A1 | 3/2010 |
| WO | 2010/038714 A1 | 4/2010 |
| WO | 2010/128084 A1 | 11/2010 |
| WO | 2011/044934 A1 | 4/2011 |
| WO | 2012/123770 A1 | 9/2012 |
| WO | 2012/143787 A1 | 10/2012 |
| WO | 2012/153179 A1 | 11/2012 |
| WO | 2013/050833 A1 | 4/2013 |
| WO | 2014/023995 A1 | 2/2014 |
| WO | 2014/184639 A1 | 11/2014 |
| WO | 2014/184643 A1 | 11/2014 |

OTHER PUBLICATIONS

Klaver et al. Appl Environ Microbiology, 1993, vol. 59, No. 4, pp. 1120-1124.*
Losada et al. Nutrition Research 2002, vol. 22, pp. 71-84.*
7th Probiotics, Prebiotics & New Foods Proceedings and Abstracts URL: http://www.probioticsprebiotics-newfood.com/pdf/7th_Probiotics_Prebiotics_Newfood.pdf> pp. 1-206, Sep. (2013).
Aloisio I., et al., "Characterization of Bifidobacterium spp. Strains for the Treatment of Enteric Disorders in Newborns," Applied Microbiology and Biotechnology, Dec. 2012, vol. 96 (6), 19 pages.
Antao E.M., et al., "The Chicken as a Natural Model for Extraintestinal Infections caused by Avian Pathogenic *Escherichia Coli* (APEC)," Microbial Pathogenesis, Nov.-Dec. 2008, vol. 45 (5-6), 9 pages.
Anukam K.C., et al., "Lactobacillus Plantarum and Lactobacillus Fermentum with Probiotic Potentials Isolated from the Vagina of Healthy Nigerian Women," Research Journal of Microbiology, 2007, vol. 2 (1), 8 pages.
Baluka et al., "PCR-Based Detection of Genes Responsible for Oxalate Detoxification in Probiotic Microorganisms," Annual Meeting of the Illinois State Academy of Sciences, 2008 Retrieved from the Internet: [https://www.eiu.edu/biology/posters/2008-11.pdf], 1 page.
Barber A.E., et al., "Strengths and Limitations of Model Systems for the Study of Urinary Tract Infections and Related Pathologies," Microbiology and Molecular Biology Reviews, Jun. 2016, vol. 80 (2), 18 pages.
Best E.L., et al., "Models for the Study of Clostridium Difficile Infection," Gut Microbes, Mar.-Apr. 2012, vol. 3 (2), 23 pages.
Busch N.A., et al., "A Model of Infected Burn Wounds Using *Escherichia Coli* O18:K1:H7 for the Study of Gram-Negative Bacteremia and Sepsis," Infection and Immunity, Jun. 2000, vol. 68 (6), 3 pages.

Chen H.L., et al., "Probiotic Lactobacillus casei Expressing Human Lactoferrin Elevates Antibacterial Activity in the Gastrointestinal Tract," Biometals, Jun. 2010, vol. 23 (3), 12 pages.
Darouiche R.O., et al., "Bacterial Interference for Prevention of Urinary Tract Infection: a Prospective, Randomized, Placebo-controlled, Double-blind Pilot Trial," Clinical Infectious Diseases: An Official Publication of the Infectious Diseases Society of America, Nov. 2005, vol. 41 (10), 4 pages.
Decision to Grant a Patent for Invention issued for Russian application No. 2013148474 filed on May 9, 2012, dated May 19, 2017, 11 pages (English Translation and Russian Original).
Decision to Grant dated Sep. 2, 2016 for Russian Patent Application No. 2014110640/05 filed on Sep. 21, 2012 on behalf of Probiotical S.P.A., 9 pages.
Douillard F.P., et al., "Comparative Genomic and Functional Analysis of 100 Lactobacillus Rhamnosus Strains and their Comparison with Strain GG," PLOS Genetics, Aug. 2013, vol. 9 (8). 15 pages.
Examination Report dated Apr. 28, 2014 for NewZealand IP No. 614002 filed on Aug. 6, 2013 in the name of Probiotical S.P.A., 2 pages.
First Examination Report dated Mar. 9, 2016 for Chilean application No. 2013002148 filed on Jul. 26, 2013, 21 pages.
Japanese Patent Office Official Action for Japanese Patent Application No. 2013550962, dated Dec. 1, 2015, 10 pages (Japanese original+ English translation).
Japanese Patent Office Official Action for Japanese Patent Application No. 2013558517, dated Mar. 3, 2015, 4 pages (Japanese original+ English translation).
Japanese Patent Office Official Action for Japanese Patent Application No. 2014509849, dated Apr. 26, 2016, 9 pages (Japanese original + English translation).
Japanese Patent Office Official Action for Japanese Patent Application No. 2014529081, dated May 31, 2016, 8 pages (Japanese original+ English translation).
Japanese Patent Office Official Action Summary for Japanese Patent Application No. 2014509850 filed on behalf of Probiotical S.P.A., dated Feb. 16, 2016, 5 pages (Japanese original + English translation).
Japanese Patent Office Official Action for Japanese Patent Application No. 2016513455, dated Jan. 16, 2018, 7 pages (English Translation+ Japanese Original).
Kizerwetter-Swida M., et al., "Selection of Potentially Probiotic Lactobacillus Strains Towards Their Inhibitory Activity Against Poultry Enteropathogenic Bacteria," Polish Journal of Microbiology, 2005, vol. 54 (4), 8 pages.
Mathews H.M., et al., "Sodium Bicarbonate as a Single Dose Antacid in Obstetric Anaesthesia," Anaesthesia, Jul. 1989, vol. 44 (7), 2 pages.
Moen S.T., et al., "Testing the Efficacy and Toxicity of Adenylyl Cyclase Inhibitors Against Enteric Pathogens Using in Vitro and in Vivo Models of Infection," Infection and Immunity, Apr. 2010, vol. 78 (4), 10 pages.
Mogna L., et al., "In Vitro Inhibition of Klebsiella Pneumoniae by Lactobacillus Delbrueckii Subsp. Delbrueckii LDD01 (DSM 22106): An Innovative Strategy to Possibly Counteract Such Infections in Humans?," Journal of Clinical Gastroenterology, Nov.-Dec. 2016, vol. 50 (Supp 2), 4 pages.
Mogna, L., et al., "Screening of Different Probiotic Strains for Their In Vitro Ability to Metabolise Oxalates: Any Prospective Use in Humans?" Journal of Clinical Gastroenterology, 2014, vol. 48, S91-S95). 5 pages.
Office Action dated Feb. 15, 2016 for Chinese Patent Application No. 201180070870.0, 15 pages (Chinese original+ English translation).
Office Action dated Mar. 25, 2016 for Chinese Patent Application No. 201280015994.3, 23 pages (Chinese original+ English translation).
Office Action for Chinese Patent Application No. 201280022854.9, dated May 17, 2016. 12 pages. (Chinese original + English translation).
Office Action dated Feb. 13, 2017 for Chinese Patent Application No. 201280022854.9 filed on May 9, 2012 in the name of Probiotical S.P.A., 12 pages (English+ Chinese).

(56) References Cited

OTHER PUBLICATIONS

Office Action for KZ Application No. 20131615.1 filed on Jan. 24, 2012 by Tagbergenova Alma Taishevna et al., dated Jul. 15, 2014, 5 pages, (Russian Original+ English Translation).
Office Action Inquiry for Russian Patent Application No. 2013144267 filed on Mar. 17, 2011 on behalf of Probiotical S.P.A. dated Mar. 12, 2015, 5 pages (English Translation).
Office Action for Russian Patent Application No. 2013137656/15(056766) filed on Jan. 24, 2012 on behalf of Probiotical S.P.A. dated Mar. 18, 2016. 10 pages (Russian original + English translation).
Office Action for Russian Patent Application No. 2014107771/10(012274) filed on behalf of Probiotical S.P.A. dated Jun. 2, 2016, 8 pages (Russian original+ English translation).
Opposition to Ecuadorian Patent Application SP201313082 on behalf of Alafar, 2015, 14 pages (Spanish original + English translation).
Ritchie J.M., "Animal Models of Enterohemorrhagic *Escherichia coli* Infection," Microbiology Spectrum, Aug. 15, 2014, vol. 2(4), 13 pages, EHEC-0022-2013.
Scardovi V., et al., "Multiple Electrophoretic Forms of Transaldolase and 6-Phosphogluconic Dehydrogenase and Their Relationships to the Taxonomy and Ecology of the Bifidobacteria," International Journal of Systematic and Evolutionary Microbiology, Original Papers Relating to Systematic Bacteriology, vol. 29 (4), Oct. 1979, 16 pages.
Shim Y.H., et al., "Antimicrobial Activity of Lactobacillus Strains Against Uropathogens," Pediatrics International, Oct. 2016, vol. 58 (10), 5 pages.
Tsai C.C., et al., "Three Lactobacillus Strains From Healthy Infant Stool Inhibit Enterotoxigenic *Escherichia Coli* Grown in Vitro," Anaerobe, Apr. 2008, vol. 14 (2), 7 pages.
Ventura M. et al., "Identification and Tracing of Bifidobacterium Species by Use of Enterobacterial Repetitive Intergenic Consensus Sequences," Applied and Environmental Microbiology, vol. 69 (7), Jul. 2003, 6 pages.
Wikipedia "Colony-Forming Unit", Downloaded from the internet Apr. 13, 2017. http://en.wikipedia.org/wiki/Colony-forming unit, 1 page.
Wiktionary "Cluster—definition" retrieved from the internet on Apr. 27, 2017 from http://web.archive.org/web/20100214060846/https://en.wiktionary.org/wiki/cluster, 4 pages.
Zarate et al., "Protective Effect of Vaginal Lactobacillus Paracasei CRL 1289 Against Urogenital Infection Produced by *Staphylococcus Aureus* in a Mouse Animal Model," Infectious Diseases in Obstetrics and Gynecology, Mar. 2007, 6 pages.
Non-Final Office Action for U.S. Appl. No. 13/982,255, filed Nov. 12, 2013 on behalf of Giovanni Mogna. dated Mar. 10, 2015, 10 pages.
Restriction Requirement for U.S. Appl. No. 13/982,255, filed Nov. 12, 2013 on behalf of Giovanni Mogna. dated Oct. 17, 2014, 6 pages.
Non-Final Office Action for U.S. Appl. No. 15/265,706, filed Sep. 14, 2016 on behalf of Probiotical S.P.A. dated Jul. 11, 2017. 13 pages.
Final Office Action for U.S. Appl. No. 15/265,706, filed Sep. 14, 2016 on behalf of Probiotical S.P.A. dated Feb. 2, 2018. 18 pages.
Non-Final Office Action for U.S. Appl. No. 14/005,821, filed Nov. 6, 2013 on behalf of Giovanni Mogna. dated Jun. 5, 2014. 30 pages.
Final Office Action for U.S. Appl. No. 14/005,821, filed Nov. 6, 2013 on behalf of Giovanni Mogna. dated Dec. 30, 2014. 29 pages.
Restriction Requirement for U.S. Appl. No. 14/116,999, filed Dec. 20, 2013 on behalf of Giovanni Mogna. dated Mar. 11, 2015. 11 pages.
Non-Final Office Action for U.S. Appl. No. 14/116,999, filed Dec. 20, 2013 on behalf of Giovanni Mogna. dated Jun. 16, 2015. 17 pages.
Non-Final Office Action for U.S. Appl. No. 14/116,999, filed Dec. 20, 2013 on behalf of Giovanni Mogna. dated Mar. 14, 2016. 23 pages.
Notice of Allowance for U.S. Appl. No. 14/116,999, filed Dec. 20, 2013 on behalf of Giovanni Mogna. dated Sep. 4, 2018. 9 pages.
Restriction Requirement for U.S. Appl. No. 14/116,996, filed Dec. 18, 2013 on behalf of Giovanni Mogna. dated Feb. 4, 2015. 10 pages.
Non-Final Office Action for U.S. Appl. No. 14/116,996, filed Dec. 18, 2013 on behalf of Giovanni Mogna. dated May 21, 2015. 18 pages.
Final Office Action for U.S. Appl. No. 14/116,996, filed Dec. 18, 2013 on behalf of Giovanni Mogna. dated Mar. 7, 2016. 18 pages.
Restriction Requirement for U.S. Appl. No. 14/344,021, filed May 9, 2014 on behalf of Giovanni Mogna. dated Aug. 14, 2015. 7 pages.
Notice of Allowance for U.S. Appl. No. 14/344,021, filed May 9, 2014 on behalf of Giovanni Mogna. dated Mar. 27, 2018. 7 pages.
Non-Final Office Action for U.S. Appl. No. 14/346,941, filed Mar. 24, 2014 on behalf of Probiotical North America Inc. dated Apr. 19, 2017. 12 pages.
Final Office Action for U.S. Appl. No. 14/346,941, filed Mar. 24, 2014 on behalf of Probiotical North America Inc. dated Jan. 22, 2018. 13 pages.
Restriction Requirement for U.S. Appl. No. 14/891,321, filed Nov. 13, 2015 on behalf of Probiotical S.P.A. dated Jun. 16, 2017. 5 pages.
Non-Final Office Action for U.S. Appl. No. 14/891,321, filed Nov. 13, 2015 on behalf of Probiotical S.P.A. dated Sep. 6, 2017. 11 pages.
Final Office Action for U.S. Appl. No. 14/891,321, filed Nov. 13, 2015 on behalf of Probiotical S.P.A. dated Apr. 25, 2018. 7 pages.
Restriction Requirement for U.S. Appl. No. 14/891,306, filed Nov. 13, 2015 on behalf of Probiotical S.P.A. dated Apr. 13, 2016. 7 pages.
Final Office Action for U.S. Appl. No. 14/891,306, filed Nov. 13, 2015 on behalf of Probiotical S.P.A. dated Jan. 18, 2018. 26 pages.
Bozzi Cionci, N., et al., "Therapeutic Microbiology: The Role of Bifidobacterium breve as Food Supplement for the Prevention/Treatment of Paediatric Diseases," Nutrients, 10, 1723, Published: Nov. 10, 2018. 27 Pages.
Decision of Rejection for Chinese Application No. 201280031191.7, dated May 12, 2020, with English translation. 14 pages.
Notice of Allowance for U.S. Appl. No. 14/116,996, filed Dec. 18, 2013 on behalf of Giovanni Mogna. dated Aug. 14, 2020. 10 Pages.
Notice of Allowance for U.S. Appl. No. 14/891,306, filed Nov. 13, 2015 on behalf of Probiotical S.P.A. dated Aug. 5, 2020. 9 Pages.
Advisory Action U.S. Appl. No. 14/344,047, filed Jul. 28, 2014 on behalf of Giovanni Mogna. Mail Date: Nov. 28, 2017. 13 pages.
Basic Microbiology, Eighth edition. Wesley Volk and Jay Brown, eds. Addison-Wesley (1997), pp. 221,344-345. 5 pages.
Bifisterol Class IIA Medical Device for Oral Use Pamphlet/Packaging from http://www.probiotical.com. 2 pages. 2015.
Bifisterol Probiotic Product Pamphlet from http://www.probiotical.com. 2 pages. 2015.
Bondarenko V. M. Molecular-cellular mechanisms of therapeutic action of probiotics. Biologicals. Prevention, diagnosis, treatment. Scientific center of expertise of medical application of the Ministry of health of the Russian Federation (Moscow) 2010, No. 1 (37) p. 31-34; 6 pages.
Botes, M., et al. "Evaluation of Enterococcus mundtii ST4SA and Lactobacillus plantarum 423 as probiotics by using a gastrointestinal model with infant milk formulations as substrate", International Journal of Food Microbiology (Dec. 2008), 128(2), 362-370. Abstract Only.
Brazilian Office Action for Brazilian Application No. BR112013028496-0 dated Oct. 17, 2019 on behalf of Probiotical S.P.A., 5 pages. Brazilian + English translation.
Brazilian Office Action for Brazilian Application No. BR112013028705-5 dated Aug. 14, 2019 on behalf of Probiotical S.P.A., 6 pages. Brazilian + English translation.
Brazilian Patent Office Official Action for Brazilian Patent Application No. BR112015027536-2 filed on behalf of Probiotical S.P.A. , dated Oct. 2, 2019, 6 pages. (Brazilian + English translation).
Chinese Patent Office First Office Action for Chinese Patent Application No. 201480027970.9. dated Jul. 3, 2018. 12 pages (Chinese Original + English translation).

(56) References Cited

OTHER PUBLICATIONS

Chinese Search Report for Chinese Application No. 201480027970.9 filed May 14, 2014 on behalf of Probiotical S.P.A. dated Jun. 21, 2018. 7 pages. (Chinese Original + English Translation).
Decision of Rejection for CN201280022854 filed on behalf of Probiotical S.P.A. on Nov. 11, 2013. dated Sep. 8, 2017. (Chinese Original + English translation). 18 pages.
Decision to Grant for Russian Patent Application No. 2014107771/10 filed Sep. 10, 2012 on behalf of Probiotical S.P.A. dated May 23, 2017. 11 pages (Russian original+ Partial English translation).
Del Piano et al., presented in the 7th Probiotics, Prebiotics & New Foods Meeting held in Rome on Sep. 8-10, 2013, published in Journal of Clinical Gastroenterology, 48/Suppl 1:S56-61,2014 (Year: 2013).
Examination Report for Indian Application No. 8722/CHENP/2013 filed on behalf of Probiotical S.P.A. dated Jul. 5, 2018. 8 Pages. (Hindi + English Translation).
Final Office Action for U.S. Appl. No. 14/113,211, filed Nov. 26, 2013, on behalf of Hoffmann-Eitle Srl. dated Sep. 28, 2018. 23 pgs.
Final Office Action for U.S. Appl. No. 14/113,211, filed Nov. 26, 2013 on behalf of Giovanni Mogna. dated Nov. 22, 2016, 12 pages.
Final Office Action for U.S. Appl. No. 14/113,211, filed Nov. 26, 2013 on behalf of Giovanni Mogna. dated Mar. 4, 2020. 25 pages.
Final Office Action for U.S. Appl. No. 14/117,003, filed Dec. 27, 2013 on behalf of Giovanni Mogna. dated Jun. 2, 2016. 11 pages.
Final Office Action for U.S. Appl. No. 16/368,655, filed Mar. 28, 2019 on behalf of Probiotical S.P.A dated Jul. 14, 2020 14 pages.
Final Office Action for U.S. Appl. No. 14/116,996, filed Dec. 18, 2013 on behalf of Probiotical S.P.A. dated Jan. 25, 2019. 29 pages.
Fourth Office Action for Chinese Patent Application No. 201280015994.3 filed on behalf of Probiotical S.P.A. dated May 22, 2018. 20 pages. (English Translation + Chinese Original).
Giglione, E., et al. "The Association of Bifidobacterium breve BR03 and B632 is Effective to Prevent Colics in Bottle-fed Infants", Journal of Clinical Gastroenterology, vol. 50 (2), S164-S167, (Nov. 2016). 4 pages.
Grill J.P., et al., "Bile Salt Toxicity to Some Bifidobacteria Strains: Role of Conjugated Bile Salt Hydrolase and pH," Canadian Journal of Microbiology, Oct. 2000, vol. 46 (10), 878-884. 7 pages.
Hearing Notice for Indian Application No. 8722/CHENP/2013 filed on behalf of Probiotical S.P.A. Date of Dispatch: Oct. 17, 2019. 3 Pages (Hindi+ English Translation).
International Preliminary Reporton Patentability for Application No. PCT/IB2012/001848 filed Sep. 21, 2012 on behalf of Probiotical S.P.A. dated Mar. 25, 2014. 4 pages. (English Only).
International Preliminary Reporton Patentability for Application No. PCT/IB2014/000731 filed May 14, 2014 on behalf of Probiotical S.P.A. dated Nov. 17, 2015. 11 pages (English Only).
International Preliminary Report on Patentability for International Application No. PCT/IB2012/000779 filed Apr. 18, 2012 on behalf of Giovanni Mogna. dated Oct. 22, 2013. 6 pages. (English Only).
International Preliminary Report on Patentability for International Application No. PCT/IB2012/001741 filed Sep. 10, 2012 on behalf of Giovanni Mogna. dated Mar. 12, 2014. 10 pages.
Jackson, S.A. et al., "Improving End-User Trust in the Quality of Commercial Probiotic Products", Frontiers in Microbiology, Apr. 2019, vol. 10, Article 739, 15 pages. http://www.frontiersin.org.
Japanese Office Action for Japanese Application No. 2014-529082 filed Mar. 7, 2014 on behalf of Probiotical S.P.A. dated Jul. 19, 2016. 13 pages (Japanese Original + English Translation).
Japanese Patent Office Decision To Grant for Japanese Patent Application No. 2016-513453 filed on behalf of Probiotical S.P.A, certification date Sep. 3, 2019, dated Sep. 10, 2019. 7 pages (Japanese + English translation).
Kaewnopparat, S., et al. "In vitro probiotic properties of Lactobacillus fermentum SK5 isolated from vagina of a healthy woman", Anaerobe (Aug. 2013), 22, 6-13. 8 pages.
Klaver F.A.M., et al., "The Assumed Assimilation of Cholesterol by Lactobacilli and Bifidobacterium Bifidum Is Due to Their Bile Salt-Deconjugating Activity," Applied and Environmental Microbiology, Apr. 1993, vol. 59 (4), 1120-1124. 5 pages.
Klemenak, M., et al.," Administration of Bifidobacterium breve Decreases the Production of TNF-a in Children with Celiac Disease," Dig Dis Sci. 60(11):3386-92, 2015. 7 pages.
Lai, et al., "Lansoprazole For The Prevention of Recurrences of Ulcer Complications From Long-Term Low-Dose Aspirin Use", N Engl J Med. 346 (26) 2002: 2033-2038.
Lee, Y.K., et al., "Handbook of Probiotics and Prebiotics", Second Edition (2009), John Wiley & Sons, Inc. pp. 4, 5 and 24. 5 pages of English copy.
Mcfarland, et al. "Strain-Specificity and Disease-Specificity of Probiotic Efficacy: A Systematic Review and Meta-Analysis", Frontiers in Medicine, vol. 5, Article 124, (May 2018), 14 pages.
Mogna, et al. "Capability of the Two Microorganisms Bifidobacterium breve B632 and Bifidobacterium breve BR03 to Colonize the Intestinal Microbiota of Children", Journal of Clinical Gastroenterology, vol. 48 (1), S37-S39, (Nov. 2014). 3 pages.
Non-Final Office Action for U.S. Appl. No. 14/113,211, filed Nov. 26, 2013 on behalf of Hoffmann-Eitle Srl. dated May 29, 2019. 29 pages.
Non-Final Office Action for U.S. Appl. No. 14/117,003, filed Dec. 27, 2013 on behalf of Giovanni Mogna. dated Oct. 14, 2015. 18 pages.
Non-Final Office Action for U.S. Appl. No. 15/265,706, filed Sep. 14, 2016 on behalf of Probiotical S.P.A.. dated Apr. 17, 2019. 27 pages.
Non-Final Office Action for U.S. Appl. No. 16/368,655 filed on behalf of Probiotical S.p.A. dated Mar. 2, 2020. 22 pages.
Non-Final Office Action for U.S. Appl. No. 14/891,306, filed Nov. 13, 2015 on behalf of Probiotical S.P.A dated May 2, 2019 25 pages.
Notice of Allowance for U.S. Appl. No. 14/116,996, filed Dec. 18, 2013 on behalf of Giovanni Mogna. dated May 6, 2020. 11 Pages .
Notice of Allowance for U.S. Appl. No. 14/116,999, filed Dec. 20, 2013, on behalf of Probiotical S.P.A. dated Dec. 26, 2018. 14 pages.
Notice of Allowance for U.S. Appl. No. 14/117,003, filed Dec. 27, 2013 on behalf of Giovanni Mogna. dated Nov. 9, 2016. 7 pages.
Notice of Allowance for U.S. Appl. No. 14/117,003, filed Dec. 27, 2013 on behalf of Giovanni Mogna. dated Jul. 6, 2017. 10 pages.
Notice of Allowance for U.S. Appl. No. 14/117,003, filed Dec. 27, 2013 on behalf of Giovanni Mogna. dated Nov. 22, 2016. 8 pages.
Notice of Allowance for U.S. Appl. No. 14/117,003. dated Nov. 24, 2017, 5 pages.
Notice of Allowance for U.S. Appl. No. 14/346,941, filed Mar. 24, 2014 on behalf of Probiotical North America Inc.. dated Apr. 8, 2019. 29 pages.
Notice of Allowance for U.S. Appl. No. 14/891,306, filed Nov. 13, 2015 on behalf of Probiotical S.P.A. dated May 22, 2020 11 pages.
Notice of Allowance for U.S. Appl. No. 14/891,306, filed Nov. 13, 2015 on behalf of Probiotical S.P.A. dated Jan. 13, 2020. 15 pages.
Notice of Allowance for U.S. Appl. No. 14/346,941, filed Mar. 24, 2014 on behalf of Probiotical North America Inc. dated Aug. 6, 2018. 8 pages.
Notice of Allowance for U.S. Appl. No. 14/116,996, filed Dec. 18, 2013 on behalf of Giovanni Mogna. dated Feb. 26, 2020. 10 Pages.
Notice of Allowance for U.S. Appl. No. 14/116,996, filed Dec. 18, 2013 on behalf of Giovanni Mogna. dated Sep. 24, 2019. 16 pages.
Notification of Reexamination for Chinese Patent Application No. CN201280022854 in the name of Probiotical S.P.A, dated Sep. 29, 2018. (Chinese Original + English Translation). 14 pages.
Office Action for Japanese Patent Application No. 2016-513453 filed on behalf of Probiotical S.P.A.. dated Jan. 9, 2018. 10 pages (Japanese Original + English Translation).
Office Action for Russian Patent Application No. 2015148750/15 filed May 14, 2014 on behalf of Probiotical S.P.A. dated Mar. 5, 2018. 19 pages (Russian Original + English Translation).
Peng F., et al., "Health Education for Kidney Diseases," Hubei Science & Technology Press, Dec. 31, 2007, p. 102.(Chinese Original + English Translation) 5 pages.

(56) References Cited

OTHER PUBLICATIONS

Preliminary office Action for Brazilian Application No. BR112013028709-8 filed on May 9, 2012 on behalf of Probiotical S.P.A. dated Aug. 13, 2019. 5 Pages (Portuguese and Informal English Translation).
Restriction Requirement for U.S. Appl. No. 14/117,003, filed Dec. 27, 2013 on behalf of Giovanni Mogna. dated Feb. 20, 2015. 9 pages.
Restriction Requirement for U.S. Appl. No. 16/368,655, filed Mar. 28, 2019 on behalf of Probiotical S.P.A. dated Oct. 10, 2019. 7 pages.
Rowe, R.C et al., "Handbook of Pharmaceutical Excipients", Chemical Industry Press, 4th Edition, pp. 692-693, (Jan. 31, 2005), 9 pages. (English + Chinese translation).
Russian Office Action for Russian Application No. 2015148752/15 filed on May 14, 2014 on behalf of Probiotical S.P.A. dated Apr. 24, 2018. 11 pages. (Russian original + English translation).
Russian Search Report for Russian Application No. 2015148750/15 filed on May 14, 2014 on behalf of Probiotical S.P.A. dated Mar. 5, 2018. 5 pages. (Russian original + English translation).
Russian Search Report for Russian Application No. 2015148752/15 filed on May 14, 2014 on behalf of Probiotical S.P.A. dated Apr. 20, 2018. 4 pages. (Russian original + English translation).
Schillinger U., et al., "Antibacterial Activity of Lactobacillus sake Isolated from Meat", Applied and Environmental Microbiology, Aug. 1989, vol. 55, No. 8, pp. 1901-1906.
Simone, et al. "The Probiotic Bifidobacterium breve B632 Inhibited the Growth of Enterobacteriaceae within Colicky Infant Microbiota Cultures", Hindawi Publishing Corporation, BioMed Research International, vol. 2014, article ID 301053 (Aug. 2014). 7 pages.
"The Language of Prevention" from National Public Health Partnership, 2006. Melbourne: NPHP. 9 pages.
"Study on Optimization of Exopolysaccharide and Characteristics of Streptococcus Thermophilus ST1," 2011.73 pages (7-8). (English Abstract).
Wang Q., et al., "Urinary Tract Infections," Shanghai Liandong Press, Jul. 31, 2001, p. 4 (original + English translation). 5 pages.
Wikipedia definition of p-value (printed on Jul. 3, 2018) 12 pages. https://en.wikipedia.org/wiki/P-value.
Wikipedia entry for "yeast", dated Mar. 1, 2011 (13 pages).
Wiktionary "Bifidogenic" Last modified Jul. 19, 2014, Retrieved from the internet on Apr. 13, 2017, from http://en.wiktionary.org/wiki/bifidogenic, 1 page.
Anukam, K.C et al., "Lactobacillus Plantarum and Lactobacillus Fermentum with Probiotic Potentials Isolated from the Vagina ofHealthy Nigerian Women.", Research Journal of Microbiology, 2(1), pp. 81-87, (2007).
Baluka, A.E.C et al., "PCR-Based Detection of Genes Responsible for Oxalate Detoxification in Probiotic Microorganisms.", Annual Meeting of the Illinois State Academy of Sciences, (http://www.eiu.edu/biology/posters/2008-11.pdf)., (2008), 1 page.
Darouiche, R.O. et al., "Bacterial Interference for Prevention of Urinary Tract Infection: A Prospective, Randomized, Placebo-Controlled, Double-Blind Pilot Trial.", Clinical Infectious Diseases, 41, pp. 1531-1534, (2005).
Mathews, H.M.L et al., "Sodium Bicarbonate as a Single Dose Antacid in Obstetric Anaesthesia.", Anaesthesia, vol. 44, pp. 590-591, (1989).
Scardovi, V et al., "Multiple Electrophoretic Forms of Transaldolase and 6-Phosphogluconic Dehydrogenase and Their Relationships to the Taxonomy and Ecology of the Bifidobacteria.", International Journal of Systematic Bacteriology, vol. 29, No. 4, pp. 312-327, (1979).
Zarate, G. et al., "Protective Effect of Vagina Lactobacillus Paracasei CRL 1289 Against Urogenital Infection Produced by *Staphyloccus Aureus* in a Mouse Animal Model", Infectious Diseases in Obstetrics and Gynecology, vol. 2007, Article ID 48358, pp. 1-6, (2007).
Final Office Action for U.S. Appl. No. 15/265,706, filed Sep. 14, 2016 on behalf of Giovanni Mogna. dated Feb. 2, 2018. 18 pages.

Non-Final Office Action for U.S. Appl. No. 14/113,211, filed Nov. 26, 2013 on behalf of Giovanni Mogna. dated Dec. 7, 2017. 19 pages.
Non-Final Office Action for U.S. Appl. No. 14/116,999, filed Dec. 20, 2013 on behalf of Giovanni Mogna. dated Jan. 5, 2018. 18 pages.
Non-Final Office Action for U.S. Appl. No. 14/116,996, filed Dec. 18, 2013 on behalf of Giovanni Mogna. dated Mar. 27, 2017. 16 pages.
Final Office Action for U.S. Appl. No. 14/116,996, filed Dec. 18, 2013 on behalf of Giovanni Mogna. dated Dec. 14, 2017. 17 pages.
Final Office Action for U.S. Appl. No. 14/344,047, filed Jul. 28, 2014 on behalf of Giovanni Mogna. dated Aug. 4, 2017. 20 pages.
Non-Final Office Action for U.S. Appl. No. 14/344,021, filed May 9, 2014 on behalf of Giovanni Mogna. dated Jul. 24, 2017. 13 pages.
Notice of Allowance for U.S. Appl. No. 14/344,021, filed May 9, 2014 on behalf of Giovanni Mogna. dated Dec. 15, 2017. 7 pages.
Non-Final Office Action for U.S. Appl. No. 14/346,941, filed Mar. 24, 2014 on behalf of Giovanni Mogna. dated Apr. 19, 2017. 12 pages.
Final Office Action for U.S. Appl. No. 14/346,941, filed Mar. 24, 2014 on behalf of Giovanni Mogna. dated Jan. 22, 2018. 13 pages.
Restriction Requirement for U.S. Appl. No. 14/891,321, filed Nov. 13, 2015 on behalf of Giovanni Mogna. dated Jun. 16, 2017. 5 pages.
Non-Final Office Action for U.S. Appl. No. 14/891,321, filed Nov. 13, 2015 on behalf of Giovanni Mogna. dated Sep. 6, 2017. 11 pages.
Final Office Action for U.S. Appl. No. 14/891,306, filed Nov. 13, 2015 on behalf of Giovanni Mogna. dated Jan. 18, 2018. 26 pages.
Canadian Office Action for CA Application No. 2,912,013 filed on May 14, 2014 on behalf of Probiotical S.P.A. dated Aug. 24, 2020. 4 pages.
Corrected Notice of Allowability for U.S. Appl. No. 14/891,306, filed Nov. 13, 2015 on behalf of Probiotical S.P.A. dated Aug. 20, 2020. 5 pages.
Korean Office Action for KR Application No. 1020157035288 filed on May 14, 2014 on behalf of Probiotical S.P.A. dated Aug. 11, 2020 8 pages (English + Original).
Brazilian Office Action for Brazilian Application No. BR112013028496-0 filed May 9, 2012 on behalf of Probiotical S.P.A. Dated: Oct. 6, 2020. Portuguese Original + English Translation. 12 Pages.
Notice of Allowance for U.S. Appl. No. 14/116,996, filed Dec. 18, 2013 on behalf of Giovanni Mogna. dated Dec. 3, 2020. 11 Pages.
Notice of Allowance (Technical Examination Report) of Sep. 14, 2020, published in Brazilian Industrial Property Journal of Sep. 29, 2020 for Brazilian Application No. BR112013028709-8 filed on May 9, 2012 on behalf of Probiotical S.P.A. 5 Pages (Portuguese + partial Eng trans.).
Notice of Allowance for U.S. Appl. No. 14/891,306, filed Nov. 13, 2015 on behalf of Probiotical S.P.A. dated Jan. 15, 2021. 11 Pages.
Brazilian Office Action for Brazilian Application No. BR112013028705-5 filed on May 9, 2012 on behalf of Probiotical S.P.A., dated Dec. 14, 2020. 6 pages. Brazilian + partial English translation.
Corrected Notice of Allowability for U.S. Appl. No. 14/116,996, filed Dec. 18, 2013 on behalf of Giovanni Mogna. dated Mar. 1, 2021.3 pages.
Patent Certificate for IN Application No. 1949/MUMNP/2013 filed on May 9, 2012 on behalf of Probiotical S.P.A. dated Feb. 9, 2021 28 pages.
Non-Final Office Action for U.S. Appl. No. 16/368,655, filed Mar. 28, 2019, on behalf of Probiotical S.p.A. dated Apr. 22, 2021. 19 pages.
Non-Final Office Action for U.S. Appl. No. 14/113,211, filed Nov. 26, 2013 on behalf of Giovanni Mogna. dated Apr. 23, 2021. 26 pages.
Shin, J.M et al., "Pharmacology of Proton Pump Inhibitors", Curr. Gastroenterol Rep., Dec. 2008, 10 (06), pp. 528-534. 11 pages.

\* cited by examiner

BACTERIAL STRAINS BELONGING TO THE GENUS *BIFIDOBACTERIUM* FOR USE IN THE TREATMENT OF HYPERCHOLESTEROLAEMIA

CROSS REFERENCE TO RELATED APPLICATIONS

The present application is the divisional application of U.S. patent application Ser. No. 14/117,003 filed on Dec. 27, 2013, which is the US national stage of International Patent Application PCT/IB2012/000907 filed on May 9, 2012 which, in turn, claims priority to Italian Patent Application MI2011A000792 filed on May 9, 2011.

The present invention relates to selected bacterial strains belonging to the genus *Bifidobacterium* for use in the treatment of hypercholesterolaemia. In particular, the present invention relates to a food composition or supplement product or medical device or pharmaceutical composition comprising said bacterial strains in association with sterols or phytosterols and/or stanols or phytostanols and/or glucomannan and/or konjac gum and/or prebiotic fibres and/or fermented red rice and/or betaglucans from oats, oat bran, barley, barley bran and/or *Aloe arborescens* gel in lyophilized form.

It is well known that all the cells of the body are capable of synthesizing cholesterol from acetyl coenzyme A, but most cholesterol is produced in the peroxisomes of liver cells, which transfer it to the blood so as to be transported throughout the body.

When we speak of "cholesterol" in medicine, we do not mean cholesterol as a chemical product, but are rather actually talking about a class of lipoproteins (chylomicrons, transport aggregates) which circulate in the blood. The concentration of the aforesaid lipoproteins is called blood cholesterol. Depending on their composition in terms of cholesterol, phospholipids, proteins, triglycerides and fatty acids, these aggregates are further distinguished in several classes (according to the specific weight, comprised between 0.98 and 1.17 $g/cm^3$): VLDL (very low density lipoproteins), IDL (intermediate density lipoproteins), LDL (low density lipoproteins), HDL2 and HDL3.

The biosynthesis of cholesterol is regulated by the intracellular concentration of cholesterol and by the hormones insulin and glucagon, so that cholesterol is synthesized only in case of need, to avoid wasting energy. In fact, a high intracellular concentration of cholesterol associated with the hormones insulin and glucagon inhibits the enzyme HMG-CoA reductase, thus blocking the biosynthesis of new cholesterol. For this reason, the amount of cholesterol synthesized is inversely proportional to the amount of cholesterol taken in through the diet.

In the case of a hypercholesterolaemic diet, the amount of cholesterol synthesized through cholesterol biosynthesis decreases, but the cholesterol test parameters can nonetheless exceed the threshold values recommended by the World Health Organization: total blood cholesterol below 200 mg/dl and a total cholesterol/HDL ratio of less than 5 (for men) and less than 4.5 (for women).

Approximately, the following are recognized:
i) Normal blood cholesterol levels, with a value of less than 200 mg/dl blood cholesterol.
ii) Mild hypercholesterolaemia, with a value comprised from 200 to 249 mg/dl.
iii) Moderate hypercholesterolaemia, with a value comprised from 250 to 299 mg/dl.
iv) Severe hypercholesterolaemia, with a value greater than 300 mg/dl.

The fact of exceeding the threshold values (200 mg/dl) of the cholesterol test parameters limits many people in the choice of foods they can eat and in the lifestyle they can maintain. These limitations/deprivations can also have consequences on the mood of the people themselves, who view themselves as deprived of the freedom of choosing what to eat since they are conscious of the fact that the choice of eating a dish with a high cholesterol content implies either a series of sacrifices in the following days or, in some cases, a sense of guilt about having "disobeyed" or contributed to increasing the blood cholesterol values.

Therefore, it would be useful and desirable to have a composition capable of normalizing the cholesterol test parameters in subjects who occasionally indulge in high-cholesterol foods.

The existence of drugs, such as statins, which inhibit endogenoous cholesterol synthesis by acting on the enzyme 3-hydroxy-3-methylglutaril-CoA reductase, an enzyme that converts molecules of 3-hydroxy-3-methylglutaril-CoA into mevalonic acid, a precursor of cholesterol, is well known.

A problem deriving from the intake of said drugs, e.g. statins, lies in the fact that by reducing the level of endogenous cholesterol said drugs contribute to increasing the biosynthesis of intracellular cholesterol.

An increase in the biosynthesis of intracellular cholesterol means that when a patient stops taking statins, for example, the biosynthesis of intracellular cholesterol is not immediately normalized (reduced) upon interruption of the intake of the statins, but rather continues as if the patient were still taking the drug (there is said to be a "past memory").

Therefore, once the intake of statins, for example, is interrupted, the biosynthesis of intracellular cholesterol takes a certain amount of time before being normalized, i.e. before reducing said biosynthesis to the levels existing before the intake of the statin-based drug began. This uncontrolled and unnecessary production of cholesterol represents a serious drawback.

Therefore, it would be desirable to have a treatment as an alternative to statins, for example, but not only. The treatment called for must be a treatment that can be freely interrupted by the subject without any further cholesterol production. In practical terms, it would be desirable to have a new treatment which, on the one hand, is capable of reducing the endogenous level of cholesterol and, on the other hand, in the event that the treatment itself is interrupted, is capable of normalizing the biosynthesis of intracellular cholesterol so as to normalize the physiological level of cholesterol.

The Applicant has provided an answer to the above-mentioned needs following an intense activity of research, at the end of which it identified, from a highly vast set of strains, a selection of bacterial strains belonging to the genus *Bifidobacterium*. Said strains exhibit a marked ability to reduce the blood cholesterol level, in particular the level of LDL cholesterol.

Figure 1:
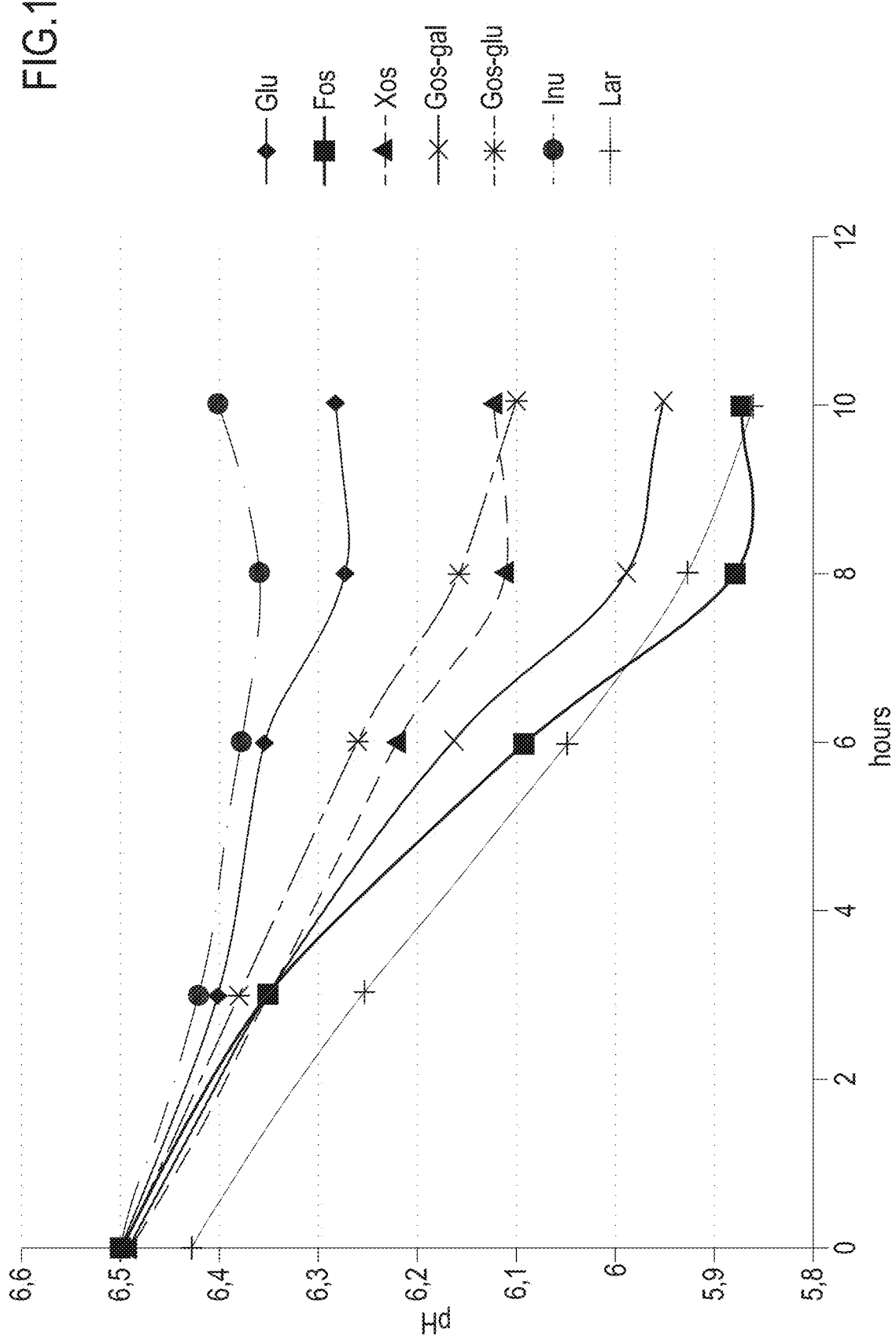
FIG. 1. Determination of acidification curves for the strain *B. longum* BL04 DSM 23233.

The subject matter of the present invention relates to a bacterial strain belonging to the genus *Bifidobacterium* and having the characteristics as disclosed in the appended claim.

Said strain belongs to the species *Bifidobacterium bifidum*. The Applicant carried out a selection on many bacterial strains belonging to the species *Bifidobacterium bifidum*. The strains selected for their properties are:

(i) *Bifidobacterium bifidum* BB06 deposited by the company Probiotical S.p.A of Novara (Italy) with the DSMZ on 29 Mar. 2011, with accession number DSM 24688.

(ii) *Bifidobacterium bifidum* MB109 deposited by the company Probiotical S.p.A of Novara (Italy) with the DSMZ on 29 Jun. 2010, with accession number DSM 23731.

The Applicant carried out a selection on many bacterial strains belonging to the species *Bifidobacterium lactis*. The strains selected for their properties are:

(i) *Bifidobacterium lactis* MB2409 deposited by the company Probiotical S.p.A of Novara (Italy) with the DSMZ on 29 Jun. 2010, with accession number DSM 23733.

(ii) *Bifidobacterium lactis* BS07 (MB243) deposited by the company Probiotical S.p.A of Novara (Italy) with the DSMZ on 29 Mar. 2011, with accession number DSM 24690.

The Applicant carried out a selection on many bacterial strains belonging to the species *Bifidobacterium breve*. The strain selected for its properties is *Bifidobacterium breve* MB113 deposited by the company Probiotical S.p.A of Novara (Italy) with the DSMZ on 29 Jun. 2010, with accession number DSM 23732.

The Applicant carried out a selection on many bacterial strains belonging to the species *Bifidobacterium infantis*. The strain selected for its properties is *Bifidobacterium infantis* BI02 (MB287) deposited by the company Probiotical S.p.A of Novara (Italy) with the DSMZ on 29 Mar. 2011, with accession number DSM 24687.

In the context of the present invention, the bacteria can be present in isolated form or with the respective supernatant. They can be present in the form of live or dead bacteria or components thereof or as a cellular extract or enzymatic extract.

The subject matter of the present invention relates to a food composition or supplement product or medical device or pharmaceutical composition having the characteristics disclosed in the appended claim.

The food composition or supplement product or medical device or pharmaceutical composition comprises a mixture of bacterial strains consisting of at least one bacterial strain belonging to the genus *Bifidobacterium* having the ability to reduce the level of blood cholesterol, in particular LDL cholesterol.

In another preferred embodiment, said at least one bacterial strain is selected from the group comprising the bacterial strains belonging to the species *Bifidobacterium bifidum*, *Bifidobacterium lactis*, *Bifidobacterium breve* and *Bifidobacterium infantis*.

The food composition or supplement product or medical device or pharmaceutical composition comprises a mixture of bacterial strains consisting of at least one bacterial strain selected from the group comprising or, alternatively, consisting of:

(1) *Bifidobacterium bifidum* BB06 (MB107) deposited by the company Probiotical S.p.A of Novara (Italy) with the DSMZ on 29 Mar. 2011, with accession number DSM 24688; and/or (2) *Bifidobacterium bifidum* MB109 deposited by the company Probiotical S.p.A of Novara (Italy) with the DSMZ on 29 Jun. 2010, with accession number DSM 23731; and/or (3) *Bifidobacterium lactis* MB2409 deposited by the company Probiotical S.p.A of Novara (Italy) with the DSMZ on 29 Jun. 2010, with accession number DSM 23733, and/or (4) *Bifidobacterium lactis* BS07 (MB243) deposited by the company Probiotical S.p.A of Novara (Italy) with the DSMZ on 29 Mar. 2011, with accession number DSM 24690; and/or (5) *Bifidobacterium breve* MB113 deposited by the company Probiotical S.p.A of Novara (Italy) with the DSMZ on 29 Jun. 2010, with accession number DSM 23732; and/or (6) *Bifidobacterium infantis* BI02 (MB287) deposited by the company Probiotical S.p.A of Novara (Italy) with the DSMZ on 29 Mar. 2011, with accession number DSM 24687.

The subject matter of the present invention relates to a food composition or supplement product or medical device or pharmaceutical composition which comprises a bacterial composition consisting of (i) at least one bacterial strain belonging to the species *Bifidobacterium bifidum* capable of adsorbing cholesterol onto its surface cell wall, and (ii) at least one bacterial strain belonging to the species *Bifidobacterium lactis, Bifidobacterium breve* or *Bifidobacterium infantis* capable of hydrolyzing bile salts at an intracellular and/or extracellular level, for use in the preventive or curative treatment of hypercholesterolaemia.

The food composition or supplement product or medical device or pharmaceutical composition is intended for use to reduce the level of LDL cholesterol in the blood. Moreover, said strain belonging to the species *Bifidobacterium bifidum* is selected from the group consisting of the bacterial strain *B. bifidum* BB06 (MB107) DSM 24688 and the bacterial strain *B. bifidum* (MB109) DSM 23731. Furthermore, said strain belonging to the species *Bifidobacterium lactis* is selected from the group consisting of the bacterial strain *B. lactis* (MB2409) DSM 23733 and the bacterial strain *B. lactis* BS07 (MB243) DSM 24690. Moreover, said strain belonging to the species *Bifidobacterium breve* is the bacterial strain *B. breve* (MB113) DSM 23732. Furthermore, said strain belonging to the species *Bifidobacterium infantis* is the bacterial strain *B. infantis* B102 (MB287) DSM 24687.

The food composition or supplement product or medical device or pharmaceutical composition further comprises a bacterial strain belonging to the species *Bifidobacterium longum* capable of producing conjugated linoleic acid (CLA) from linoleic acid (LA). Moreover, said strain belonging to the species *Bifidobacterium longum* is *Bifidobacterium longum* (BL04) DSM 23233.

The subject matter of the present invention relates to a food composition or supplement product or medical device or pharmaceutical composition that comprises a bacterial composition consisting of at least one bacterial strain belonging to the species *Bifidobacterium bifidum*, at least one bacterial strain belonging to the species *Bifidobacterium lactis* and at least one bacterial strain belonging to the species Bidifobacterium *longum*, for use in the preventive or curative treatment of the hypercholesterolaemia. Said strain belonging to the species *Bifidobacterium bifidum* is selected from the group consisting of the bacterial strain *B. bifidum* BB06 (MB107) DSM 24688 and the bacterial strain *B. bifidum* (MB109) DSM 23731; preferably it is the bacterial strain *B. bifidum* (MB109) DSM 23731. Moreover, said strain belonging to the species *Bifidobacterium lactis* is selected from the group consisting of the bacterial strain *B.*

*lactis* (MB2409) DSM 23733 and the bacterial strain *B. lactis* BS07 (MB243) DSM 24690; preferably it is the bacterial strain *B. lactis* (MB2409) DSM 23733. Moreover, said strain belonging to the species *Bifidobacterium longum* is *Bifidobacterium longum* (BL04) DSM 23233.

In the food composition or supplement product or medical device or pharmaceutical composition there is further present at least one vegetable substance selected from the group comprising sterols or phytosterols, stanols or phytostanols, glucomannan, konjac gum and/or at least one prebiotic fibre selected from the group comprising fructo-oligosaccharides—FOS, galacto-oligosaccharides—GOS, xylo-oligosaccharides—XOS, inulin, larch fibres or arabinogalactan and/or fermented red rice and/or betaglucans from oats, oat bran, barley, barley bran and/or *Aloe arborescens* gel in lyophilized form.

In the food composition or supplement product or medical device or pharmaceutical composition there is further present: (i) at least one vegetable substance selected from the group comprising sterols or phytosterols and/or stanols or phytostanols in association with at least one vegetable substance selected from the group comprising glucomannan, konjac gum, fermented red rice, betaglucans from oats, oat bran, barley, barley bran and *Aloe arborescens* gel in lyophilized form;

(ii) at least one vegetable substance selected from the group comprising sterols or phytosterols and/or stanols or phytostanols in association with at least one vegetable substance selected from the group comprising glucomannan, konjac gum, fermented red rice, betaglucans from oats, oat bran, barley, barley bran and *aloe arborescens* gel in lyophilized form in association with at least one prebiotic fibre selected from the group comprising FOS, GOS, XOS, inulin, larch fibre or arabinogalactan.

Advantageously, the food composition or supplement product or medical device or pharmaceutical composition comprises a mixture of bacterial strains comprising or, alternatively, consisting of at least two bacterial strains. At least a first strain must have a mechanism of non-specific adsorption of cholesterol (cholesterol adsorption onto the surface cell wall of the bacterium), whereas at least a second strain must have a specific BSH (Bile Salts Hydrolase) enzymatic activity.

The food composition or supplement product or medical device or pharmaceutical composition of the present invention has valid application in the preventive or curative treatment of disorders or pathologies connected with high blood cholesterol levels, i.e. cholesterol levels exceeding 200 mg/dl; and in the treatment of hypercholesterolaemia.

The above-described compositions, to which the present invention relates, have valid application in reducing the level of blood cholesterol, in particular LDL cholesterol.

In a preferred embodiment, the food composition or supplement product or pharmaceutical composition of the present invention further comprises at least one vegetable substance selected from the group comprising or, alternatively, consisting of sterols or phytosterols and/or stanols or phytostanols. The amount of sterols/stanols per daily dose of composition must be greater than 0.8 g, preferably from 1 g to 3 g, for example, from 1.5 to 2.0 g.

In a preferred embodiment, the food composition or supplement product or medical device or pharmaceutical composition of the present invention further comprises at least one vegetable substance selected from the group comprising or, alternatively, consisting of glucomannan, konjac gum, fermented red rice, betaglucans from oats, oat bran, barley, barley bran and *Aloe arborescens* gel in lyophilized form. The amount of glucomannan/konjac gum per daily dose of composition must be greater than 4 g, preferably from 5 g to 10 g, for example, from 6 to 8 g.

If betaglucans from oats, oat bran, barley or barley bran are used, an intake of 3 grams per day must be ensured in order to contribute to maintaining normal blood cholesterol levels.

In a preferred embodiment, the food composition or supplement product or medical device or pharmaceutical composition of the present invention further comprises at least one vegetable substance selected from the group comprising or, alternatively, consisting of sterols and stanols in association with at least one other substance of vegetable origin selected from the group comprising or, alternatively, consisting of glucomannan and konjac gum. The daily recommended doses are indicated above.

In a preferred embodiment, the food composition or supplement product or pharmaceutical composition of the present invention further comprises at least one prebiotic fibre selected from the group comprising or, alternatively, consisting of FOS, GOS, XOS and inulin.

In a preferred embodiment, the food composition or supplement product or pharmaceutical composition of the present invention further comprises at least one vegetable substance selected from the group comprising or, alternatively, consisting of sterols and stanols in association with at least one prebiotic fibre selected from the group comprising or, alternatively, consisting of FOS, GOS, XOS and inulin.

In a preferred embodiment, the food composition or supplement product or pharmaceutical composition of the present invention further comprises at least one vegetable substance selected from the group comprising or, alternatively, consisting of glucomannan and konjac gum in association with at least one prebiotic fibre selected from the group comprising or, alternatively, consisting of FOS, GOS, XOS and inulin.

In a preferred embodiment, the food composition or supplement product or pharmaceutical composition of the present invention further comprises at least one vegetable substance selected from the group comprising or, alternatively, consisting of sterols and stanols in association with at least one vegetable substance selected from the group comprising or, alternatively, consisting of glucomannan and konjac gum in association with at least one prebiotic fibre selected from the group comprising or, alternatively, consisting of FOS, GOS, XOS, inulin.

The above-described compositions have valid application in the treatment of healthy subjects having a blood cholesterol level that is within the normal range, but which occasionally, due to the intake of a quantity of fats in the diet, can increase, giving rise to "temporary" hypercholesterolaemia. In this case, the intake, by these subjects, of a composition according to the present invention can bring the blood cholesterol level back within the normal range, since there is a reduction in excess cholesterol.

Moreover, the above-described compositions also have valid application in the treatment of subjects who normally have a high blood cholesterol level. In this case, the intake, by these subjects, of a composition according to the present invention can limit the increase in the blood cholesterol level.

As shown in the acidification curves that follow, the strain BL04 prefers a vegetable substance such as FOS, larch fibres or arabinogalactan and GOS-Gal, the strain MB2409 prefers a vegetable substance such as FOS and GOS-Gale and the strain MB109 prefers a vegetable substance such as FOS and inulin.

Experimental Part

The Applicant engaged in intense research activity with the aim of selecting the bacterial strains.

In Vivo Study

A total of 32 rats were housed in cages. After several days of acclimatization to the habitual diet (T0), the rats all began to receive the same 100% hypercholesterolemizing diet. After 15 days of this diet (T15), the rats were randomly divided into 4 subgroups (8 rats per subgroup). The rats began receiving differentiated treatments from T15 to T45. These treatments continued for 30 days until sacrifice (T45):

Group 1:
30% hypercholesterolemizing diet and *Lactobacillus reuteri* NCIMB 701359 (Kandler et al.; 1982), $1 \times 10^9$/day (reference). This strain is known for its ability to lower cholesterol levels (reference);

Group 2:
30% hypercholesterolemizing diet and mixture of probiotics [*B. lactis* MB2409 DSM 23733 ($0.33 \times 10^9$/day), *B. breve* MB113 DSM 23732 ($0.33 \times 10^9$/day) and *B. bifidum* MB109 DSM 23731 ($0.33 \times 10^9$/day)];

Group 3:
30% hypercholesterolemizing diet (control).

The daily dose per rat was 1 ml of a suspension containing ($1 \times 10^9$ CFU/ml) of the bacterial strains indicated above. The dose was administered to the rats through a gastric probe.

Blood samples were taken at T0, T15 and T45 after fasting. The serum was separated from the blood obtained and the following serum parameters were determined: a) LDL cholesterol, b) HDL cholesterol, c) total cholesterol and d) triglycerides.

Phases of the Study

Phase I. Normal preliminary diet for all rats for 7 days (T-7).

Phase II. 100% hypercholesterolemizing diet for all rats from day zero (T0) to the fifteenth day (T15).

Phase III. Differentiated diet, as described above, for the 4 groups from the sixteenth to the forty-fifth day (T45).

Experimental Results

1) Change in Body Weight

The first parameter examined was the ponderal growth of the rats in order to verify a correct food intake. The data demonstrate that the rats took in food in a correct manner.

2) Effect of the Hypercholesterolemizing Diet

Since all the rats received the same diet in this first phase, they were all grouped together. Then a comparison was made among the LDL cholesterol, HDL cholesterol, total cholesterol and blood triglyceride levels at time zero (T0) and after 15 days (T15). The HDL/LDL ratio was also calculated, see Table 1.

TABLE 1

| Blood parameters | T0 | T15 |
|---|---|---|
| LDL cholesterol (mg/dl) | 18.52 ± 1.07 | 22.31 ± 3.86° |
| HDL cholesterol (mg/dl) | 65.22 ± 3.10 | 21.85 ± 4.50* |
| HDL/LDL | 3.54 ± 0.25 | 1.00 ± 0.22* |

Statistical analysis was performed with the Student's t-test:
°$p < 0.01$;
*$p < 0.001$.

The data provided in Table 1 show that the hypercholesterolemizing diet brought about a significant increase in LDL cholesterol (bad cholesterol) and an even more significant decrease in HDL cholesterol (good cholesterol). The HDL/LDL ratio, which in normal conditions should be greater than 3, was decreased by the hypercholesterolemizing diet.

3) Effect of the Different Treatments (Groups 1-3) on LDL Cholesterol

Treatments 1 and 2 (Groups 1 and 2) brought about a significant reduction in LDL cholesterol ($p < 0.001$) compared to the values at T15. In treatment 3 (Group 3), based only on a 30% hypercholesterolemizing diet, the LDL levels did not change compared to T15.

The amount of cholesterol was reduced through two mechanisms:

i) Mechanism 1: Non-specific cholesterol adsorption (onto the surface cell wall of the bacterium)

ii) Mechanism 2: Specific enzymatic activity of BSH (Bile Salts Hydrolase).

The Applicant carried out screening on a highly vast group of bacteria by evaluating the intracellular activity of BSH.

Practically speaking, each bacterial strain was cultured overnight in MRS culture medium+cysteine, 0.05% weight/volume, and was then centrifuged in order to collect a pellet of cells. This pellet was washed twice with a 0.1 M pH 6 sodium phosphate buffer in order to eliminate the extracellular BSH.

The cells were resuspended in 1 ml of pH 6 sodium phosphate buffer; lysed with glass beads via three 5-minute Vortex cycles at maximum speed at 4° C. and incubated with ice for 10 minutes. At the end of the third cycle, the sample was centrifuged at 13000 rpm for 5 minutes and all cellular debris and macromolecules were precipitated so that the supernatant, which also contains the proteins, could be used.

The supernatant underwent analysis to quantify the total proteins contained in it.

For this purpose, the Lowry method was used to determine the total amount of protein present in the extract. Practically speaking, one millilitre of Lowry reagent is added to 200 microlitres of extract, appropriately diluted.

Stock Solutions:
Lowry A: ($Na_2CO_3$ in 0.1 M NaOH (Autoclave),
Lowry B: $CuSO_4$ 1% in $H_2O$ (Sterilize by filtration),
Lowry C: 2% Na—K tartrate tetrahydrate in $H_2O$ (Sterilize by filtration).

Lowry reagent (per 50 ml-50 samples): Lowry A 49 ml+Lowry B 0.5 ml+Lowry C 0.5 ml.

200 µl of appropriately diluted sample+1 ml of Lowry reagent are combined at room temperature. They are left to incubate for 10 minutes at room temperature and then 100 microlitres of Folin-Cicalteau reagent diluted 1:1 in water is added. After 30 minutes' incubation, absorbance is measured at 500 nm. The data obtained are interpolated along a regression line with BSA. Then the total protein content of the extract is determined and expressed in mg/ml. The specific activity of BSH is titrated (units of BSH/mg of total protein) so as determine the portion of proteins present in the cellular extract which possesses BSH enzymatic activity.

For this purpose, 20 microlitres of a substrate containing taurodeoxycholic acid (TDCA)—TCDA sample—or glycocholic acid (GCA)—GCA sample—is added to the 20 microlitres of the above-described extract at a concentration of 200 mM. 360 microlitres of 0.1 M pH 6 sodium phosphate buffer is added. The experimental blank is represented by 20 microlitres of extract and 380 microlitres of 0.1 M pH 6 sodium phosphate buffer—blank sample.

The samples (TDCA sample, GCA sample and blank sample) are incubated at 37° C. This is repeated for the extract obtained from each strain. After 10 and 30 minutes of incubation, 100 microlitres of the above-described samples is collected and 100 microlitres of TCA (15% trichloroacetic acid) is added to precipitate the proteins. This is followed by 5 minutes' centrifugation at 13000 rpm in order to obtain an acidic mixture and the supernatant, which will contain the amino acids glycine and taurine, is collected.

50 microlitres of acidic mixture (for each acidic mixture obtained, i.e. blank sample, TDCA sample and GCA sample) collected at 10 and 30 minutes were analysed as such and diluted 1:5. In detail, the as such samples were evaluated using the ratios of 50 microlitres of acidic mixture and 950 microlitres of ninhydrin mixture, whereas the 1:5 dilution was evaluated by adding 10 microlitres of acidic mixture to 40 microlitres of demineralised water and adding 950 microlitres of ninhydrin mixture. The ninhydrin mixture was prepared as follows: 2 millilitres of 1% ninhydrin in a 0.5 M pH 5.5 citrate buffer; 4.8 millilitres of glycerol and 0.8 millilitres of 0.5 M pH 5.5 citrate buffer. The samples were boiled for 14 minutes and cooled for 3 minutes in water. The absorbance of each sample was read at 570 nanometres.

Quantifying the taurine and glycine requires a specific calibration curve at a standard concentration of taurine or glycine.

HPLC Operating Conditions:
Column: Zorbax Eclipse,
Flow rate: 0.2 ml/min,
Injection: 1 µl,
$\lambda$=200 nm,
Solvent: A=dd $H_2O$; B=ACN,
Gradient: B % T(min); 10%, 5 min; 100%, 30 min; 100%, 50 min; 10%, 55 min.
Retention time: GCA (MW=464):33.04 min; CA (MW=407):35.41 min
MS (Mass Spectroscopy) Operating Conditions:
Polarity: negative,
Ac. Time: 300,
Capillary current: 3500 V,
Nebulizer: 30 psi,
Dry gas: 8.0 l/min,
Dry temp.: 325° C.,
T(min): 0-30, 30-40, 40-55.

A calculation is made of the conversion %, i.e. of how much CA and GCA is present, in order to determine the presence of extracellular BSH.

Therefore, the 32 initial strains were screened considering the value of intracellular BSH (Lowry method and ninhydrin assay) and bioconversion of GCA into CA–extracellular BSH (HPLC chromatography+MS), see Table 2.

TABLE 2

| Bacterium | % Bioconversion (BSH extracellular activity) | | % average GCA bioconversion | average BSH intracellular activity vs. GCA | Std Dev. |
|---|---|---|---|---|---|
| L. reuteri NCIMB 701359 | 98 | 82.7 | 90.4 | 1.12 | 0.13 |
| B. lactis DSM 24690 | 100 | 100 | 100 | 0.59 | 0.15 |
| B. lactis DSM 23733 | 79.8 | 63.9 | 71.9 | 0.77 | 0.20 |
| B. bifidum DSM 23731 | 64.2 | 71.2 | 67.7 | 0.10 | 0.03 |
| B. breve DSM 23732 | 14.7 | 14.7 | 14.7 | 1.18 | 0.29 |
| B. infantis DSM 24687 | 6.6 | 6.9 | 6.8 | 0.67 | 0.06 |
| B. Bifidum DSM 24688 | — | — | — | 0.15 | 0.07 |

Determination of the Units of BSH Enzymatic Activity Per ml of Extract:

U/ml=micromoles of taurine or glycine released per minute/ml=[[Abs 570 of the unknown sample–Abs 570 of the blank]/10 minutes]·1/[(1.25× 1000)·(dilution factor 1 or 5)]

The BSH units (U)/ml of extract are converted into BSH units (U)/mg of total proteins based on the total protein concentration determined using the Lowry method.

At the end of this screening carried out on all the strains (by determination of the specific activity of BSH (Lowry and ninhydrin) a further analysis was conducted, consisting in the determination of GCA biotransformation with whole cells, since it represents "an extracellular activity".

Practically speaking, an overnight broth culture in MRS+ 0.05% cysteine weight/volume is carried out and then the OD at 600 nanometres is measured in order to standardize the cellular concentration.

A blank containing MRS+0.05% cysteine is prepared. 20 microlitres of a 200 mM solution of glycocholic acid (GCA) is added to 1 ml of each sample; then follows incubation at 37° C. for 20 minutes. Subsequently, 100 microlitres is collected and 100 microlitres of 15% trichloroacetic acid is added to interrupt the reaction. Then the samples are centrifuged at 12000 rpm for 5 minutes so as to separate the whole cells and proteins; they are diluted 25 times with demineralised water and injected into HPLC-MS to calculate the conversion % compared to the blank sample.

The strains were subsequently tested in order to determine their ability to reduce cholesterol by adsorption.

The cholesterol adsorption capacity was evaluated by culturing the strains in MRS medium+cysteine, to which 100 milligrams/litre of cholesterol was added. The cultures were incubated at 37° C. for 48 hours. At 24 and 48 hours after the start of incubation, samples were taken and the cholesterol remaining in the supernatant was analyzed by HPLC. The cholesterol adsorbed onto the cells was calculated and compared to a non-inoculated control (MRS medium+cysteine+100 mg/l of cholesterol). The % of cholesterol adsorbed was also considered in relation to the optical density of the culture (% of cholesterol adsorbed/OD), as this ratio expresses the cell's ability to adsorb the cholesterol onto its membrane. The cholesterol concentrations of the unknown samples were determined by means of a calibration curve with known cholesterol concentrations (from 0.00 mg/l to 100 mg/l).

HPLC Method
Column: Zorbax Eclipse XBD-C18 rapid resolution HT 4.6×50 mm 1.8 um,
Mobile phase: ACN,
DAD flow: 200 nm,
Rt cholesterol: 4.0 min
Culture Conditions
Medium
Glucose: 20 g/l,
Bacto proteose peptone no. 3, 10 g/l, Bacto beef extract: 10 g/l,
Bacto yeast extract: 5 g/l,
Sodium acetate 5 g/l,
$K_2HPO_3$: 2 g/l,
Ammonium citrate: 2 g/l,
$MgSO_4$: 0.1 g/l,
$MnSO_4$: 0.05 g/l,
Cysteine: 0.5 g/l,
Tween 80—cholesterol mixture
Autoclave at 110° C. for 30 minutes.
Growth Conditions
10% inoculation from overnight culture,
T=37° C.
Anaerobic conditions in gas,
Initial cholesterol 0.08 g/l
Time=18 hours
The cholesterol adsorption values are shown in Table 3.

TABLE 3

| Bacterium | OD | | % Adsorption | | % Adsorp/OD | | |
|---|---|---|---|---|---|---|---|
| | 1 | 2 | 1 | 2 | 1 | 2 | Avg. |
| L. reuteri NCIMB 701359 | 6.5 | 5.5 | 19.1 | 18.5 | 2.9 | 3.4 | 3.1 |
| B. bifidum DSM 24688 | 1.6 | 1.5 | 55.9 | 43.5 | 34.4 | 29.9 | 32.2 |
| B. bifidum DSM 23731 | 2.3 | 3.4 | 49.4 | 46.9 | 21.1 | 14.0 | 20.1 |
| B. lactis DSM 23733 | 2.7 | 2.2 | 18.6 | 17.7 | 6.8 | 8.2 | 7.5 |
| B. breve DSM 23732 | 1.0 | 1.3 | 6.9 | 8.9 | 7.3 | 6.6 | 7.0 |
| B. infantis DSM 24687 | 10.4 | 9.8 | 32.9 | 28.1 | 3.2 | 2.9 | 3.0 |
| B. lactis DSM 24690 | 2.1 | 2.2 | 18.4 | 13.0 | 8.8 | 6.0 | 7.4 |

The strain B. bifidum BB06 (MB107) DSM 24688 and the strain B. bifidum MB109 DSM 23731 show a high cholesterol adsorption capacity.
These two strains absorb a large amount compared to the reference L. reuteri NCIMB 701359.

In a preferred embodiment, the composition of the present invention comprises or, alternatively, consists of at least one strain having a high cholesterol adsorption capacity, selected from the group comprising or, alternatively consisting of B. bifidum BB06 (MB107) DSM 24688 and B. bifidum MB109 DSM 23731, which show a high cholesterol adsorption capacity, in association with at least one strain having an intracellular and/or extracellular BSH activity, selected from the group comprising or, alternatively, consisting of B. lactis MB2409 DSM 23733, B. breve MB113 DSM 23732, B. infantis BI02 (MB287) DSM 24687 and B. lactis BS07 (MB243) DSM 24690. Said composition can further comprise sterols and/or stanols and/or glucomannan and/or konjac gum and/or prebiotic fibres, as described above.

In a preferred embodiment, the composition of the present invention comprises or, alternatively, consists of at least one strain having a high cholesterol adsorption capacity, selected from the group comprising or, alternatively consisting of B. bifidum BB06 (MB107) DSM 24688 and B. bifidum MB109 DSM 23731, which show a high cholesterol adsorption capacity, in association with at least one strain having a BSH intracellular and/or extracellular activity, selected from the group comprising or, alternatively, consisting of B. lactis MB2409 DSM 23733 (intracellular and extracellular activity of BSH) and B. breve MB113 DSM 23732 (high intracellular activity of BSH). Advantageously, said composition comprises the strain B. bifidum MB109 DSM 23731 in association with B. lactis MB2409 DSM 23733. Said composition can further comprise sterols and/or stanols and/or glucomannan and/or konjac gum and/or prebiotic fibres, as described above.

In a preferred embodiment, the composition comprises, or alternatively consists of, B. bifidum MB109 DSM 23731 in association with B. lactis MB2409 DSM 23733. Said composition can further comprise sterols and/or stanols and/or glucomannan and/or konjac gum and/or prebiotic fibres, as described above.

The above-described compositions, to which the present invention relates, have valid application for reducing the level of blood cholesterol, in particular LDL cholesterol.

The above-described compositions, to which the present invention relates, have valid application in the preventive or curative treatment of disorders or pathologies connected with high blood cholesterol levels, cholesterol levels above 200 mg/dl; and in the treatment of hypercholesterolaemia.

Clinical Study

A clinical effectiveness study was conducted using a placebo tablet containing fructo-oligosaccharides (FOS) and silicon dioxide (total powder/capsule=280.6 mg) and a tablet containing B. lactis MB 2409 DSM23733, B. bifidum MB 109 DSM 23731 and B. longum BL 04 DSM 23233 and silicon dioxide (total powder/capsule=280.6 mg).

Substantially, two strains with hypocholesterolemizing activity and the strain that best converted linoleic acid (LA) into conjugated linoleic acid (CLA) were combined.

Type of study: double-blind randomized crossover versus placebo. The crossover was planned to take place after 75 days (15 days with 2 capsules/day+60 days with 1 capsule/day). The total duration of the study was 150 days. Load guaranteed at the end of the period: 1 billion/strain/capsule. The dosage provided for in the study for each treatment (active or placebo) was the following: 2 capsules/day for the first 15 days, 1 capsule/day for the next 60 days; after the crossover, again 2 capsules/day for the first 15 days, 1 capsule/day for the next 60 days. The clinical study confirmed the effectiveness of the tested bacterial composition in reducing the blood cholesterol level by as much as 25%.

Figure 2:
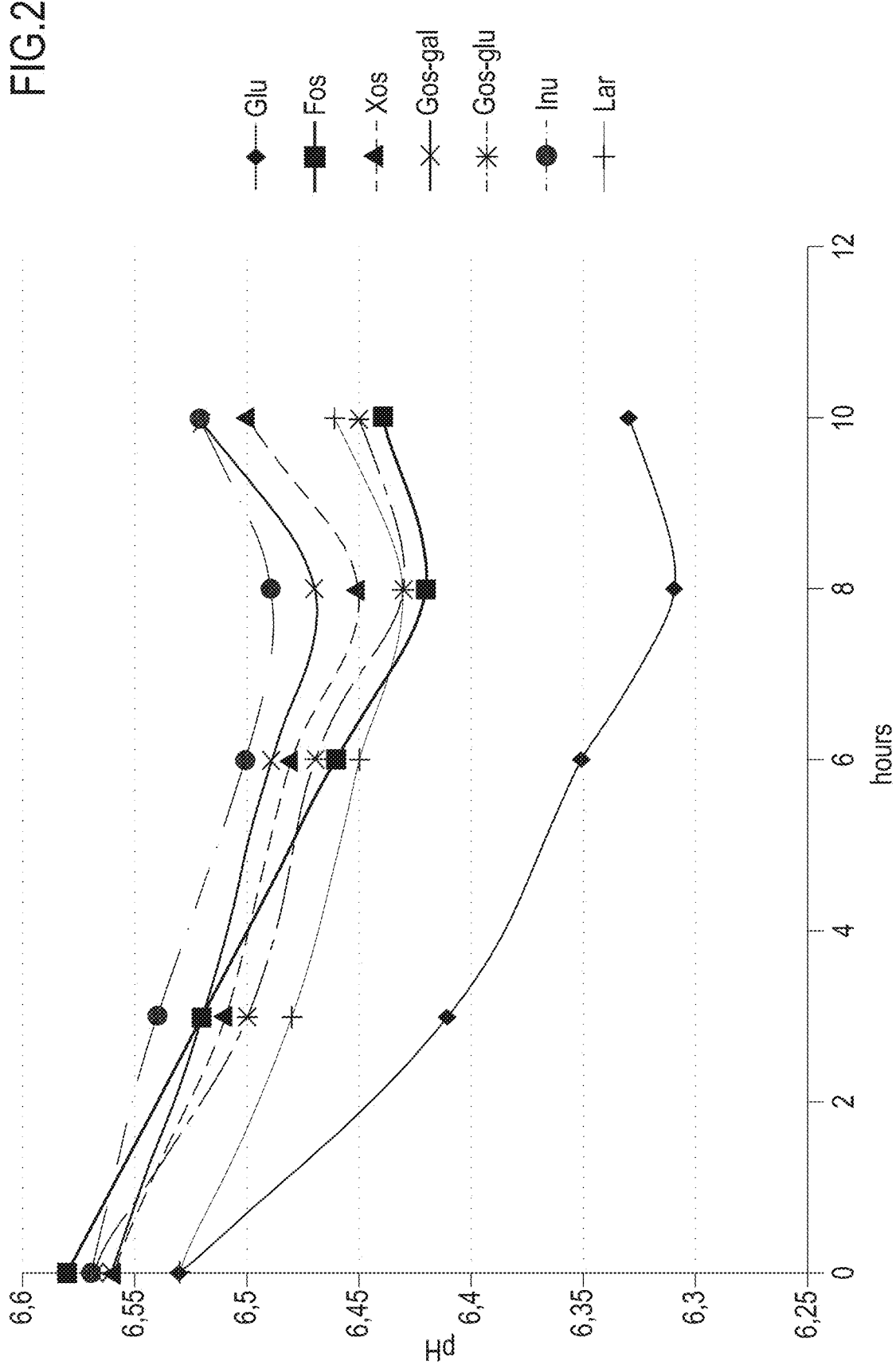
FIG. 2. Determination of acidification curves for the strain *B. lactis* MB2409 DSM 23733.
Figure 3:
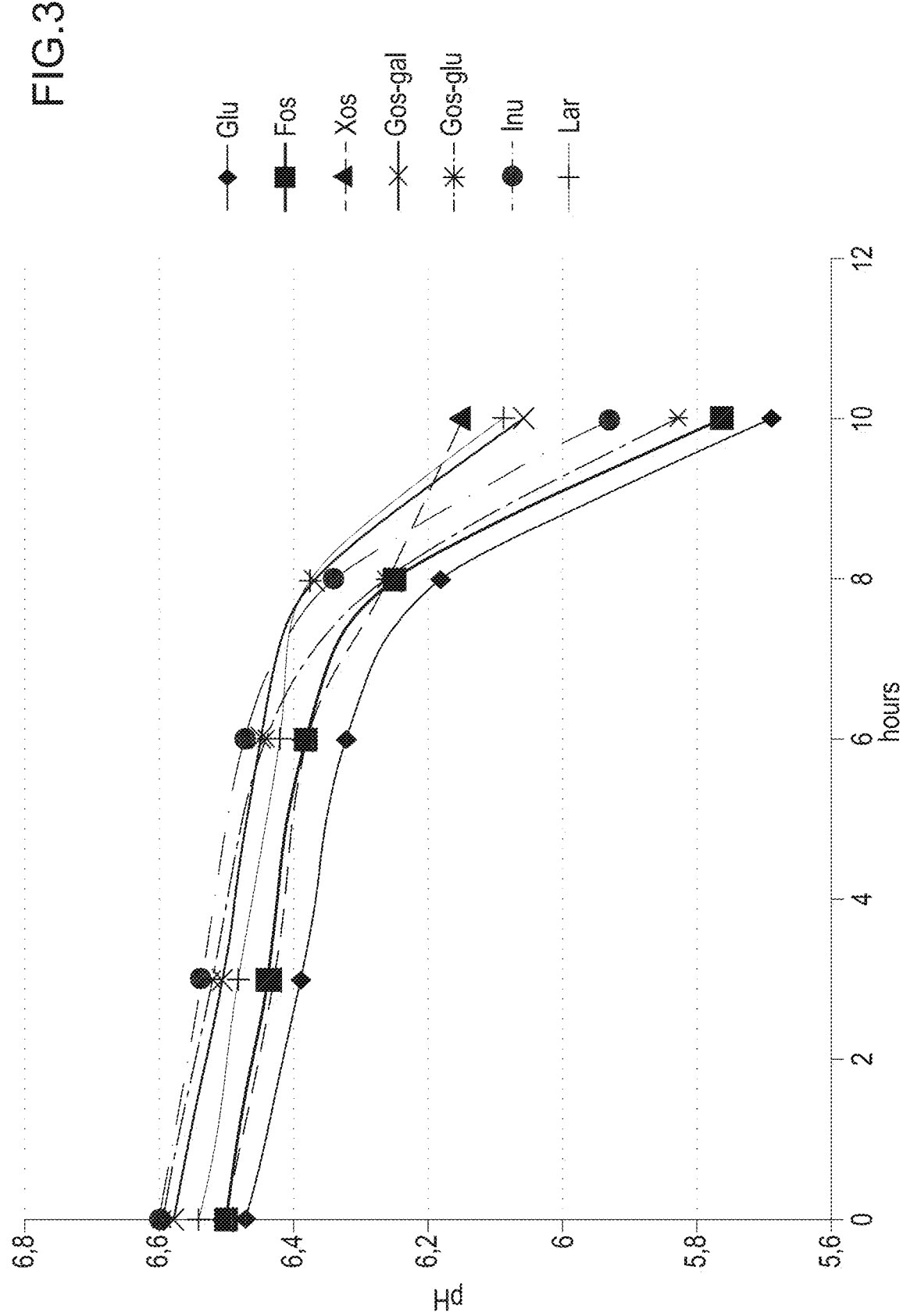
FIG. 3. Determination of acidification curves for the strain *B. bifidum* MB109.

Determination of Acidification Curves for the Strains B. bifidum MB109 DSM 23731, B. lactis MB2409 DSM 23733 and B. longum BL04 DSM 23233 (Tables 4, 5, 6 and FIGS. 1, 2, 3).

The strains MB109, MB2409 and BL04 were reactivated before the experiment by subculture in TPY+1% Cys-HCl and incubated under anaerobiosis at 37° C. The reactivation steps were repeated three times before the experiment with overnight incubation. At the end of the third reactivation step the cells were pelleted, washed with sterile water and resuspended prior to inoculation into the fibre-supplemented media. The media used are based on sugar-free MRS (carbon sources) supplemented respectively with:

Glucose (solution sterilized by heat treatment, 121° C. 15'), control medium.
FOS (solution sterilized by filtration, 0.20 µl filter).
GOS-Glu—Galacto-oligosaccharides with glucose residue (solution sterilized by filtration, 0.20 µl filter).
GOS-Gal—Galacto-oligosaccharides with galactose residue (solution sterilized by filtration, 0.20 µl filter).
XOS (solution sterilized by filtration, 0.20 µfilter).
Larex—larch fibre or arabinogalactan (solution sterilized by heat treatment, 121° C. 15').

Inulin (solution sterilized by heat treatment, 121° C. 15').

The final concentration of carbon sources for all media was 20 g/l. The media thus composed were then inoculated with 4% of the strains MB109, MB2409 and BL04 (with the addition of 1% Cys-HCl) and incubated at 37° C. under aerobiosis. At time 0 and at 3, 6, 8 and 10 hours the pH values were measured in order to construct the acidification curves shown in the graphs.

TABLE 4

|      |         | 0    | 3    | 6    | 8    | 10   |
|------|---------|------|------|------|------|------|
| BL04 | Glu     | 6.5  | 6.4  | 6.35 | 6.27 | 6.28 |
|      | Fos     | 6.5  | 6.35 | 6.09 | 5.88 | 5.87 |
|      | Xos     | 6.49 | 6.35 | 6.22 | 6.11 | 6.12 |
|      | Gos-gal | 6.49 | 6.35 | 6.16 | 5.99 | 5.95 |
|      | Gos-glu | 6.5  | 6.38 | 6.26 | 6.16 | 6.1  |
|      | Inu     | 6.5  | 6.42 | 6.38 | 6.36 | 6.4  |
|      | Lar     | 6.43 | 6.25 | 6.05 | 5.92 | 5.86 |

TABLE 5

|        |         | 0    | 3    | 6    | 8    | 10   |
|--------|---------|------|------|------|------|------|
| MB2409 | Glu     | 6.53 | 6.41 | 6.35 | 6.31 | 6.33 |
|        | Fos     | 6.58 | 6.52 | 6.46 | 6.42 | 6.44 |
|        | Xos     | 6.56 | 6.51 | 6.48 | 6.45 | 6.5  |
|        | Gos-gal | 6.56 | 6.52 | 6.49 | 6.47 | 6.52 |
|        | Gos-glu | 6.57 | 6.5  | 6.47 | 6.43 | 6.45 |
|        | Inu     | 6.57 | 6.54 | 6.5  | 6.49 | 6.52 |
|        | Lar     | 6.53 | 6.48 | 6.45 | 6.43 | 6.46 |
|        |         | 0    | 3    | 6    | 8    | 10   |

TABLE 6

|       |         | 0    | 3    | 6    | 8    | 10   |
|-------|---------|------|------|------|------|------|
| MB109 | Glu     | 6.47 | 6.39 | 6.32 | 6.18 | 5.69 |
|       | Fos     | 6.5  | 6.44 | 6.38 | 6.25 | 5.76 |
|       | Xos     | 6.5  | 6.43 | 6.38 | 6.26 | 6.15 |
|       | Gos-gal | 6.58 | 6.51 | 6.45 | 6.37 | 6.06 |
|       | Gos-glu | 6.6  | 6.52 | 6.44 | 6.26 | 5.83 |
|       | Inu     | 6.6  | 6.54 | 6.47 | 6.34 | 5.93 |
|       | Lar     | 6.54 | 6.48 | 6.42 | 6.37 | 6.09 |

The invention claimed is:

1. A medicament comprising a bacterial composition comprising:
    at least one bacterial strain belonging to the species *Bifidobacterium bifidum* capable of absorbing cholesterol onto its surface cell wall selected from the group consisting of the bacterial strain *B. bifidum* BB06 (MB107) DSM 24688 and the bacterial strain *B. bifidum* MB109 DSM 23731, and
    at least one bacterial strain belonging to the species *Bifidobacterium lactis*, *Bifidobacterium breve* or *Bifidobacterium infantis* capable of hydrolyzing bile salts on an intracellular and/or extracellular level,
    the bacterial composition in an effective amount for preventive or curative treatment of hypercholesterolaemia in a subject.

2. The medicament of claim 1, wherein said at least one bacterial strain belonging to the species *Bifidobacterium bifidum* is the bacterial strain *B. bifidum* MB109 DSM 23731.

3. The medicament of claim 1, wherein said at least one bacterial strain belonging to the species *Bifidobacterium breve* is the bacterial strain *B. breve* (MB113) DSM 23732.

4. The medicament of claim 1, wherein said at least one bacterial strain belonging to the species *Bifidobacterium infantis* is the bacterial strain *B. infantis* B102 (MB287) DSM 24687.

5. The medicament of claim 1 further comprising a bacterial strain belonging to the species *Bifidobacterium longum* capable of producing conjugated linoleic acid (CLA) from linoleic acid (LA).

6. The medicament of claim 5, wherein said bacterial strain belonging to the species *Bifidobacterium longum* is *Bifidobacterium longum* BL04 DSM 23233.

7. The medicament of claim 1 further comprising:
    at least one vegetable substance selected from the group comprising sterols or phytosterols, stanols or phytostanols, glucomannan, konjac gum,
    at least one prebiotic fibre selected from the group comprising fructo-oligosaccharides—FOS, galacto-oligosaccharides—GOS, xylo-oligosaccharides—XOS, inulin, larch fibre or arabinogalactan,
    fermented red rice,
    betaglucans from oats, oat bran, barley, barley bran, and/or
    *Aloe arborescens* gel in lyophilized form.

8. The medicament of claim 2 further comprising:
    at least one vegetable substance selected from the group comprising sterols or phytosterols, stanols or phytostanols, glucomannan, konjac gum,
    at least one prebiotic fibre selected from the group comprising fructo-oligosaccharides—FOS, galacto-oligosaccharides—GOS, xylo-oligosaccharides—XOS, inulin, larch fibre or arabinogalactan,
    fermented red rice,
    betaglucans from oats, oat bran, barley, barley bran, and/or
    *Aloe arborescens* gel in lyophilized form.

9. The medicament of claim 1, wherein said bacterial strain belonging to the species *Bifidobacterium lactis* is *Bifidobacterium lactis* MB2409 DSM 23733.

10. The medicament of claim 1, wherein the bacterial composition comprises *Bifidobacterium bifidum* MB109 DSM 23731 and *Bifidobacterium lactis* MB2409 DSM 23733.

11. The medicament of claim 10, further comprising *Bifidobacterium breve* MB113 DSM 23732.

12. The medicament of claim 10, further comprising *Bifidobacterium longum* BL04 DSM 23233.

* * * * *